United States Patent [19]

Burmeister

[11] Patent Number: 5,378,454
[45] Date of Patent: Jan. 3, 1995

[54] COMPOSITION AND PROCESS FOR PERMANENT WAVING

[75] Inventor: Frederick H. Burmeister, Rumson, N.J.

[73] Assignee: John Paul Mitchell Systems, Santa Clarita, Calif.

[21] Appl. No.: 819,085

[22] Filed: Jan. 9, 1992

[51] Int. Cl.$^6$ ............................ A61K 7/06; A61K 7/09
[52] U.S. Cl. ................................ 924/70.5; 424/70.2; 132/205
[58] Field of Search .................... 424/70, 71, 72; 132/205

[56] References Cited

U.S. PATENT DOCUMENTS

| | | | |
|---|---|---|---|
| 3,768,490 | 10/1973 | Kalopissis | 424/72 |
| 4,134,411 | 1/1979 | Yamazaki | 424/72 |
| 4,158,704 | 5/1979 | Baer | 132/204 |
| 4,913,900 | 4/1990 | Kolc | 424/72 |
| 5,068,102 | 11/1991 | Tennigkeit | 424/72 |

FOREIGN PATENT DOCUMENTS 40693A 11/1976 Germany ............... 424/72

Primary Examiner—D. Gabrielle Phelan
Assistant Examiner—Sally Gardner
Attorney, Agent, or Firm—Kalish & Gilster

[57] ABSTRACT

A waving lotion for use in an exothermic permanent wave comprising an activator in an amount sufficient to provide an exothermic reaction, with an effective perming amount of a reducing agent, wherein the reducing agent is a combination of a more active reducing agent and a less active reducing agent in a ratio necessary to effect a reduction in hair damage, wherein the less active reducing agent is an ester of thioglycolic acid.

2 Claims, No Drawings

COMPOSITION AND PROCESS FOR PERMANENT WAVING

THE FIELD OF THE INVENTION

The present invention relates to the permanent waving of hair. It particularly relates to a waving lotion and a process for using it in exothermic permanent waving. The permanent wave lotion of the present invention comprises an activator and a reducing agent containing a combination of a more active reducing agent and a less active reducing agent, wherein the less active reducing agent is an ester of thioglycolic acid. When the activator and the reducing agent are combined in the appropriate proportions, an exothermic permanent wave is produced.

BACKGROUND OF THE INVENTION

The activity or effectiveness of hair shaping preparations is based mainly on the inclusion therein of an agent for softening and relaxing the keratin protein present in hair by reducing the disulfide (S—S) linkages of keratin which covalently link adjacent polypeptide chains (K). The hair fiber is wound on rods to achieve the desired waving effect or manipulated into a straightened condition and allowed to remain wetted with the reducing lotion for a desired period, after which the reducing lotion is rinsed off and finally oxidized with a neutralizing solution or air oxidized.

Basically, hair is softened and swelled by the use of a mild alkaline reducing agent. Cleavage of at least some of the disulfide bonding to form the corresponding cystine residue is necessary to allow for molecular rearrangement which takes place during the hair fiber molding operation. The reductive fission of hair disulfides generally causes reddening of the scalp area and damage to the hair fiber, particularly hair which has been bleached, tinted or otherwise damaged. Current hair structure altering lotions which provide relaxation of imposed stress include aqueous solutions of alkaline mercapto compounds, sulfites or bisulfites at a pH of between 4 and 10. In order to obtain a permanent effect, particularly in hair straightening, it is often necessary to introduce the active agent in relatively high concentrations with the result that the reducing lotion is provided at almost the limit of its physiological compatibility or tolerability.

Damage to hair is increased where heat waving, as opposed to cold waving, is employed. Of the reducing agents currently in use, the thioglycolates or thioglycolic acid, dithioglycolic acid and mercapto compounds such as ammonium thioglycolate, glyceryl monothioglycolate, mercaptopropionic acid and mercaptoethyl amine are most often employed in the professional waving or hair straightening of the present invention. In lieu of the heat waving or cold waving, the oxidizing waving of the present invention can be effected by oxidizing the mercaptan with an agent, such as hydrogen peroxide, an iodate or a bromate. This oxidizing solution is typically called an activator.

The reducing agent used in exothermic perms is typically a mercaptan (RSH), such as ammnonium thioglycolate (ATG). The chemistry involved in the reaction of a mercaptan with the cystine disulfide bonds (KSSK) in the hair fiber to foden a disulfide, such as dithioglycolate and a keratin residue is illustrated by the following chemical equation:

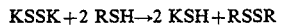

The reduced keratin is rebonded with the hair in a curled configuration to effect a permanent set. This rebonding is accomplished by the action of a chemical oxidation agent, commonly referred to as the permanent wave neutralizer. Typically, the oxidizing agents used in most neutralizers are hyrodgen peroxide and sodium bromate. The chemical oxidation (neutralization) reaction is illustrated in the following reaction:

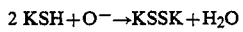

The exothermic reaction of the present invention is illustrated in the following reaction:

The di-thio formed acts to form a reverse equilibrium reaction which serves to significantly slow the reduction of the keratin to effect a "stop action" of the permanent waving process. This provides better control of the perming effect.

U.S. Pat. No. patent 4,793,994 discloses a cold wave permanent wherein a N-alkyl lactam is incorporated into a hair perming lotion. One of the effects of the addition of the lactam is a conditioning effect on the hair. The permanent wave composition contains a waving solution, which is a reducing solution that can contain ammonium thioglycolate (ATG) and/or glyceryl monothioglycolate (GMT). GMT is known to be a less active reducing agent and is suitable for bleached, permed or damaged hair. The permanent wave composition contains a neutralizing solution containing hydrogen peroxide. This lactam may be used in cold or hot waves.

U.S. Pat. No. 4,158,704 discloses a method of permanent waving which eliminates the subjective judgment of the operator in determining the conditions for waving. This method is used with cold or hot waves, wherein the waving lotion is a reducing lotion which may contain AGT and/or GMT. A neutralizing solution is used containing an oxidizing agent, such as peroxide. The method involves a numerical rating the concentration of the waving solution, the pH of the solution, the condition of the hair and the porosity of the hair. Based on an evaluation of the above four parameters, the time and the temperature of the perm is determined.

U.S. Pat. No. 4,963,349 discloses a permanent wave solution employing a 1,3-alkyldiol in its reducing solution. The alcohol solution provides a permanent wave solution employing ATG at a pH in the same acidic range as the isoelectric point of hair (pH 3 to 5), or a five minute permanent wave with either an acid or alkaline solution. The use of GMT is discouraged as an "expensive chemical which must be packaged separately." The perms are hot or cold waves.

U.S. Pat. No. 4,273,143 discloses a permanent wave solution that can be used in conjunction with an exothermic wave, having a waving lotion suitable for simultaneous use on both bleached and unbleached hair containing a lipoidal alkyl chain having ten or more carbon atoms and a disulfide derivative of a mercaptan with a substituent group. The preferred compounds contain a quaternary ammonium group and a dithio derivative of a thioglycolate.

None of the above references disclose the present permanent wave solution for exothermic permanent waving.

THE PRESENT INVENTION

The present invention is a waving lotion for use in exothermic permanent waving comprising an activator in an amount sufficient to provide an exothermic reaction with an effective perming amount of a reducing agent wherein the reducing agent contains a combination of a more active reducing agent and a less active reducing agent in a ratio necessary to effect a reduction in hair damage, wherein the less active reducing agent is an ester of thioglycolic acid.

DETAILED DESCRIPTION OF THE PRESENT INVENTION

The permanent waving lotion of the present invention comprises an activator, a more active reducing agent and a less active reducing agent. The activator causes an exothermic reaction to be effected when the activator is mixed with the waving lotion by oxidizing the mercaptan with an oxidizing agent, such as hydrogen peroxide, an iodate or a bromate. The preferred activator is hydrogen peroxide, which is easier to handle and more predictable in use. It is prepared as an aqueous solution to deliver in the range of about 0.01 to about 0.02 mole hydrogen peroxide to 80.0 g of waving lotion. Typically, the aqueous solution, which is added to the reducing lotion, contains about 4.1 to 4.5 weight % hydrogen peroxide. Below about 0.01 mole of hydrogen peroxide, insufficient dithoglycolate is produced from the ATG reaction with the keratin to produce sufficient warming to accelerate the reaction and provide sufficient stop action to protect the hair from over-processing and damage. Above 0.02 mole, the temperature rise would be excessive to the point of burning the scalp, and additionally, excessive dithioglycolate production would severely limit the reduction of the hair, resulting in little or no perming effect. [The preferred range of hydrogen peroxide is about 0.012 to 0.013 mole providing a 10° to 15° C. temperature increase, and providing adequate dithioglycolate to provide a perming effect and a stop action.] The aqueous solution can also contain a surfactant, such as Brookswax NI (a registered trademark of Brooks Industries), a fatty alcohol-/ethyoxylated fatty alcohol emulsifying wax to impart viscosity control and minimal lipid conditioning properties to the hair. The aqueous peroxide solution is pH adjusted in the range of about 3.8 to 4.2 with phosphoric acid or other acids such as, but not limited to, citric acid, hydrochloric acid or sulfuric acid.

The reducing agent is typically prepared in a reducing (waving) lotion. Suitable reducing agents that are more active include ATG, thioglycolic acid, mercaptoethyl amine and mercaptopropionic acid. The preferred reducing agent is ATG. The amount of ATG in the reducing lotion is in the range of about 0.03 to about 0.16 molar as thioglycolic acid. The preferred range is about 0.10 to 0.11 molar. At a higher concentration than about 0.16 molar, a reduced effectiveness of the stop action chemistry is observed, resulting in over-processing of and, possibly, damage to the hair. At a lower concentration than about 0.03 molar, little or no peking effect is observed. The reducing lotion typically has a pH in the range of about 4.0 to 10.5. A buffer, such as ammnonium bicarbonate may be used to maintain the desired pH. The preferred pH is in the range of about 8.5 to 9.5. At a pH lower than 8.5, the effectiveness of waving is reduced as the rate of reduction is decreased. At a pH higher than 9.5, irritation of the scalp may occur, and the stop action effect will diminish.

The reducing lotion is generally employed with an alkali having a dissociation constant less than $5 \times 10^{-3}$. Suitable compounds for alkalization include ammnonia, ammonium hydroxide, sodium hydroxide, ethanol amine, diisopropanol amine and an alkali metal salt of an amino acid, e.g. glycine, lysine or guanidine. Alkali in a concentration of between about 0.5 and about 10.0% is normally used.

Other additives which may be employed include catalysts for self-neutralizing permanent wave lotions, opacifiers to promote creamy appearance and fragrance to mask the odor of ammnonia and thiol. A native protein such as a soluble glycoprotein, or a hydrolysed protein, may also be added to the reducing lotion to moisturize and condition the hair. A preferred glycoprotein is Glyprosol 20, a registered trademark of Brooks Industries, Inc., having a molecular weight of about 10,000, a protein content of about 10% and an oligosaccharide content of about 8%.

The reducing lotions of the present invention are generally employed as about 10 to 98% solids in aqueous solutions of deionized water. The preferred range is from about 20 to 90 weight % water.

Conditioners are typically added to permanent wave lotions to minimize the damage done by the permanent waving. Fatty acid polypeptide condensates, oxyethylated fatty alcohols and oxyethylated alkyl phenols have been employed as conditioners and emollients to minimize hair damage. However, these conditioning agents only minimally protect against hair damage and do not provide a sufficient moisture barrier to eliminate dryness and splitting at the distal ends of the hair fiber when processed with the reducing lotion. The present invention provides an agent that reduces hair damage unique to exothermic permanent waves in the form of a less active reducing agent. The less active reducing agent is the ester of thioglycolic acid. Suitable less active reducing agents are lower alkyl, hydroxy-lower alkyl, and polyhydroxy-lower alkyl esters wherein the alkyl group contains from 1 to 5 carbon atoms, such as ethyl thioglycolate, methyl thioglycolate, hydroxyethyl thioglycolate, hydroxypropyl thioglycolate, glyceryl thioglycolate and the like. The preferred conditioner is glyceryl thioglycolate.

The ester of thioglycolic acid is added to the more active reducing agent and the activator to provide an exothermic waving lotion with a "stop-action" effect. The amount of thioglycolate ester added to the waving lotion to provide a molar ratio of ester to ATG in the range of approximately 1.5:1.0 to 2.5:1.0. At ratios of less than about 1.5:1.0, the resulting permed hair may be more coarse and dry to the touch. At ratios greater than about 2.5 to 1.0, softer curls with less body may result. The amount of activator added to the waving lotion is in the range of about 10 to 15 mmoles. This produces about 10 to 15 mmoles of dithioglycolate and consumes about 20 to 30 mmoles of ATG. The resulting mixture of ATG, dithioglycolate and thioglycolate ester results in adequate reduction of the hair and protection from over processing by exerting a backward force on the equilibrium of the reduction of the hair, causing a stop action. The addition of more than 15 mmoles of activator produces excessive heat, excessive dithioglycolate, and leaves insufficient ATG to drive the reduction reaction. The addition of less than 10 mmoles of activator produces insufficient heat and insufficient dithioglycolate to protect the hair against overprocessing.

The hair can be prerinsed with water or the waving lotion applied directly on the hair wound rods or in a straightened condition for softening and relaxation of the hair fiber. In this relaxed state, the hair fiber, wound on rods or straightened according to the desired structure is heated by the exothermic nature of the perm in the range of about 10° to 15° C., for a period of about 5 to 25 min. The waving lotion is water rinsed from the hair and the disulfide bonds are reformed by air oxidation or by the application of an oxidizing lotion which sets the hair, called a neutralizing solution. Suitable oxidizing agents include hydrogen peroxide, potassium bromate, sodium bromate, sodium perborate and potassium percarbonate. The oxidizing agents are typically employed as a 1 to 2 weight % active aqueous solution. Hydrogen peroxide is the preferred oxidizing agent.

EXAMPLE OF THE INVENTION

The following example is for illustrative purposes only and is not intended to limit the claims of the invention. All parts are by weight unless otherwise indicated.

The Activator

The activator contains the following components:

| Demineralized Water | 85.0% |
|---|---|
| Brookswax NI | 3.0% |
| Hydrogen Peroxide (35%) | 12.0% |

The water is heated to 70° C. and the Brookswax NI dispersed in it. The solution is cooled to 40° C. Slowly the peroxide is added, and the pH is adjusted, if necessary, with phosphoric acid, in the range of about 3.8 to 4.2. The viscosity is a minimum of about 8000 cps and the final peroxide content is about 4.1 to 4.3%.

The Reducing Lotion

The more active reducing agent (ATG) is prepared in a lotion containing the following weight % of components:

| Demineralized water | 63.75 |
|---|---|
| Ammonium thioglycolate | 20.0 |
| Ammonium Hydroxide, 26–28% | 7.0 |
| Ammonium Chloride | 2.0 |
| Sequestering Agent | 0.25 |
| Polysorbate-20 | 5.0 |
| Fragrance | 1.0 |
| Soluble Glycoprotein | 1.0 |

The water and sequestering agent, e.g., Hamp-ol are blended until dissolved. The soluble glycoprotein, e.g., Glyprosol PM is added to the solution and mixed until dissolved. The fragrance and polysorbate are mixed together and set aside. The ammonium thioglycolate, ammonium chloride, ammonium hydroxide and fragrance/polysorbate blend are blended in order, mixing well between each addition.

The Less Active Reducing Agent

The less active reducing agent is an 80% solution of glyceryl thioglycolate in anhydrous glycerin.

The Waving Lotion

The less active reducing agent (26 to 28 g) is gently mixed with 80 g of the reducing lotion. To that mixture is added 10 g of the activator, and gently mixed, thereby forming the waving lotion. The final analysis of the waving lotion indicated:

| Temperature rise | 10 to 15° C. |
|---|---|
| Total Thioglycolate | 18.0 to 19.0% |
| Free Thioglycolate | 16.0 to 17.0% |
| Dithioglycolate | 1.5 to 2.0% |
| Ammonia | 0.9 to 1.1% |
| pH | 8.2 to 8.6 |

The Neutralizer

The neutralizer is made of the following formula:

| Demineralized water | 93.0% |
|---|---|
| Silicone Emulsion | 1.0% |
| Hydrogen Peroxide (35%) | 6.0% |

The silicone emulsion is dispersed in the water at room temperature (25° C.). The peroxide is slowly added, and the pH is adjusted with phosphoric acid as needed to maintain a pH in the range of about 3.8 to 4.2. The final solution contains about 1.9 to 2.1% peroxide.

The Perm Procedure

The hair is saturated with water, allowed to drip dry, and then sectioned into about 25 sections. The distal ends of each section are wrapped in porous end papers and rolled on permanent hair setting rods. The waving lotion is applied to the hair and allowed to remain on the hair for a period of about 5 to 25 minutes, after which the rolled hair is thoroughly rinsed with water and allowed to drip dry. The neutralizing lotion is uniformly applied to saturate the hair, and allowed to remain on the hair for a period of about 3 to 10 min. The hair is rinsed and the rods removed.

I claim:

1. A waving lotion for use in exothermic permanent waving comprising an activator in an amount sufficient to provide an exothermic reaction with an effective perming amount of a reducing agent, and said reducing agent, wherein said reducing agent contains a combination of a more active reducing agent in a reducing lotion and a less active reducing agent in a ratio necessary to effect a reduction in hair damage, wherein the more active reducing agent is more active in reducing keratin protein than the less active reducing agent, wherein the activator is hydrogen peroxide and is prepared in an aqueous solution to deliver in the range of about 0.01 mole to 0.02 mole in 80 g of waving lotion, the more active reducing agent is ammonium thioglycolate and the concentration of the ammonium thioglycolate present in the reducing lotion is in range of about 0.03 to about 0.16 molar, and the less active reducing agent is glyceryl thioglycolate and is present in the waving lotion in a molar ratio with the more active reducing agent in the range of about 1.5:1.0 to 2.5:1.0.

2. A method for permanent waving comprising applying the waving lotion of claim 1 to rolled hair, allowing the lotion to remain on the hair for a period of about 5 to 25 min, rinsing the hair, and neutralizing the hair.

* * * * *